US012616530B2

(12) United States Patent
Sanford

(10) Patent No.: US 12,616,530 B2
(45) Date of Patent: May 5, 2026

(54) KNEE ARTHROPLASTY COMBINATION VALIDATION INSTRUMENT AND BONE REMOVAL TOOL

(71) Applicant: Orthosoft ULC, Montreal (CA)

(72) Inventor: Adam H. Sanford, Minneapolis, MN (US)

(73) Assignee: Orthosoft ULC

( * ) Notice: Subject to any disclaimer, the term of this patent is extended or adjusted under 35 U.S.C. 154(b) by 343 days.

(21) Appl. No.: 18/538,933

(22) Filed: Dec. 13, 2023

(65) Prior Publication Data

US 2024/0252257 A1     Aug. 1, 2024

Related U.S. Application Data

(60) Provisional application No. 63/442,030, filed on Jan. 30, 2023.

(51) Int. Cl.
| | |
|---|---|
| *A61B 34/30* | (2016.01) |
| *A61B 17/16* | (2006.01) |
| *A61B 34/00* | (2016.01) |
| *A61B 34/20* | (2016.01) |
| *A61B 90/00* | (2016.01) |

(52) U.S. Cl.
CPC .......... *A61B 34/25* (2016.02); *A61B 17/1675* (2013.01); *A61B 34/30* (2016.02); *A61B 2034/2055* (2016.02); *A61B 2034/2072* (2016.02); *A61B 2090/061* (2016.02); *A61B 2090/3916* (2016.02); *A61B 2090/3937* (2016.02)

(58) Field of Classification Search
CPC .............. A61B 17/157; A61B 17/1675; A61B 17/1659; A61B 2034/2055; A61B 2034/2072; A61B 2090/3937; A61B 34/20
See application file for complete search history.

(56) References Cited

U.S. PATENT DOCUMENTS

2008/0009697 A1 *   1/2008   Haider ................... A61B 34/30
600/407

* cited by examiner

*Primary Examiner* — Samuel S Hanna
(74) *Attorney, Agent, or Firm* — SCHWEGMAN LUNDBERG & WOESSNER, P.A.

(57) ABSTRACT

The present subject matter provides an orthopedic instrument may include a first end portion, a handle portion and an optical tracker. The first end portion is configured as a validation device having at least a first surface configured to validate a first resected surface of a bone of the knee. The first end portion has one or more surfaces with a plurality of teeth configured to remove material from the first resected surface. The handle portion is coupled to the first end portion. The optical tracker is coupled to the handle portion.

7 Claims, 14 Drawing Sheets

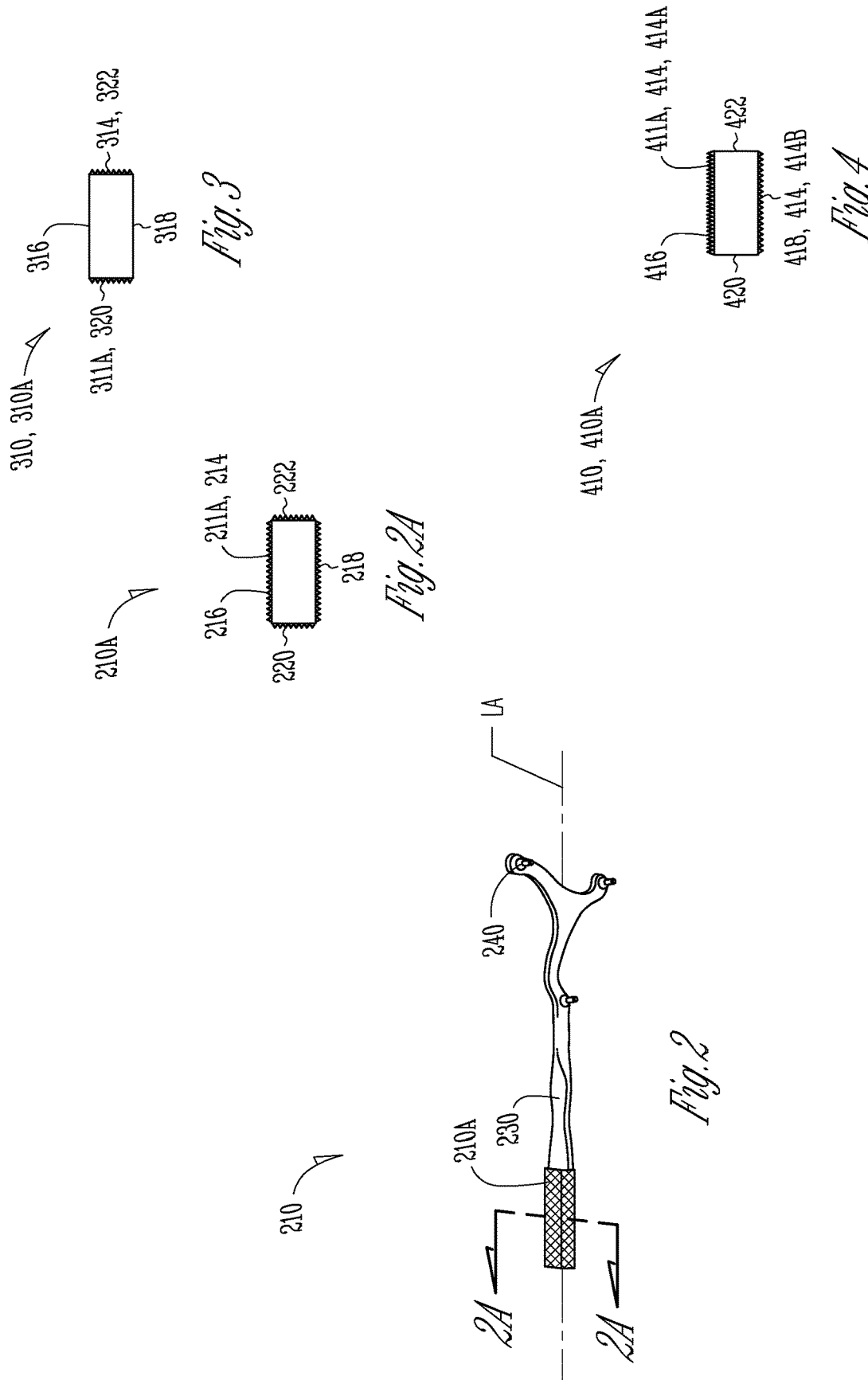

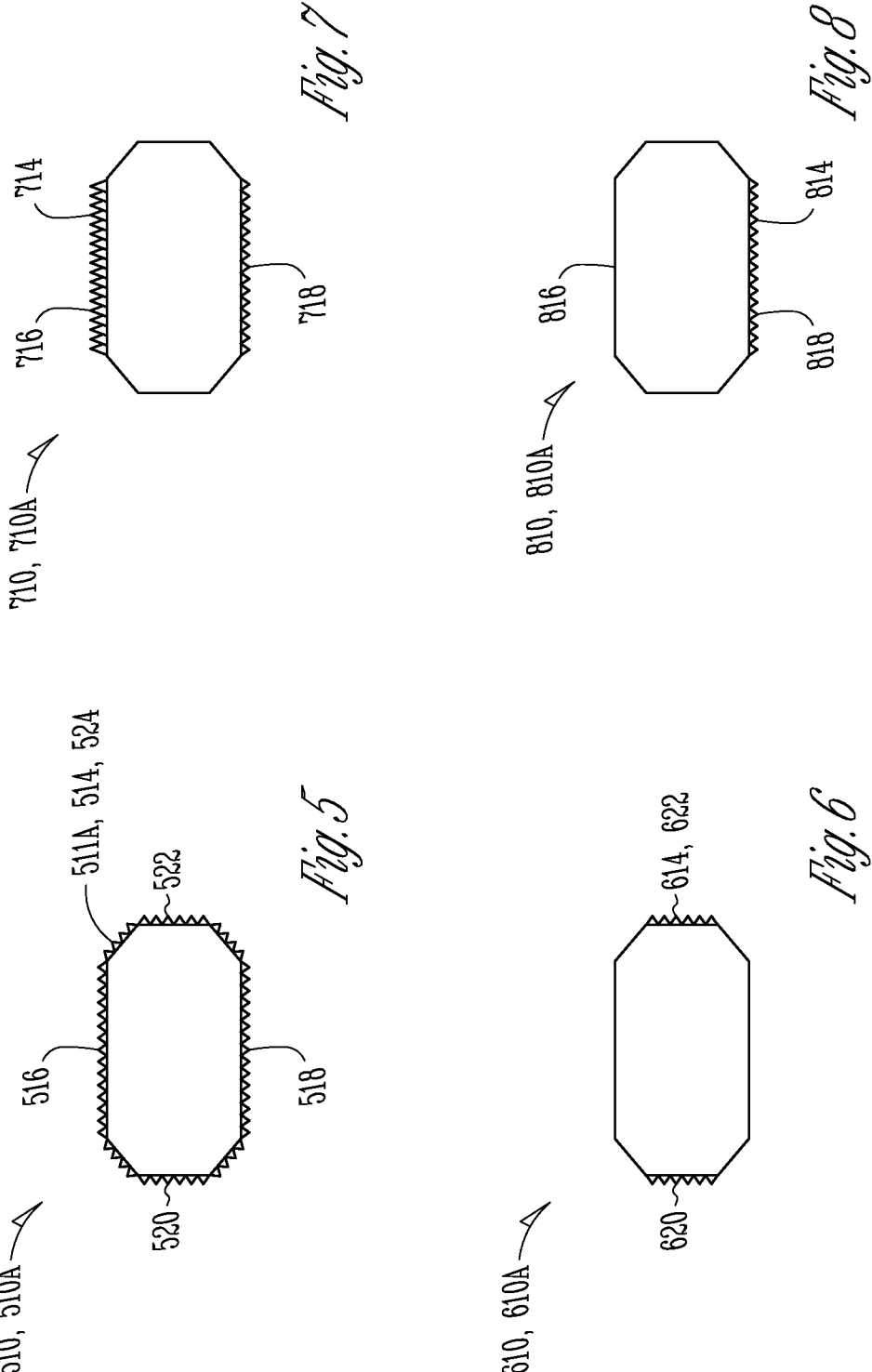

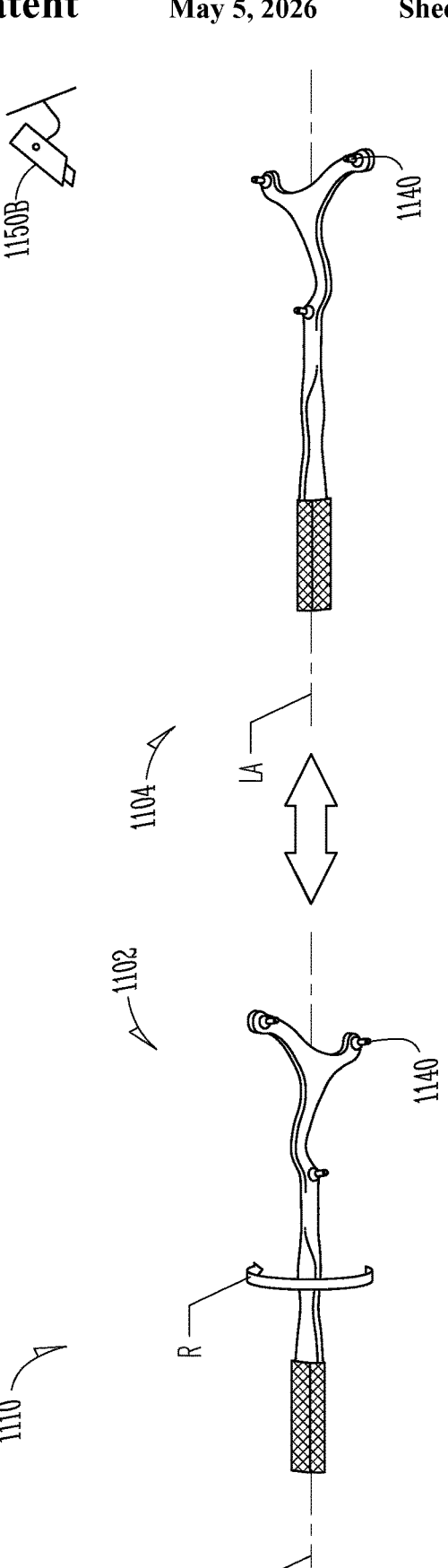
*Fig. 11*

KEEL BROACH VALIDATION:

SHIFT POSITION OF BROACH PRIOR TO STRIKING

1804

1806

1840

1800

1802

112

KNEE ARTHROPLASTY COMBINATION VALIDATION INSTRUMENT AND BONE REMOVAL TOOL

CLAIM OF PRIORITY

This application claims the benefit of U.S. Provisional Patent Application Ser. No. 63/442,030, filed on Jan. 30, 2023, the benefit of priority of which is claimed hereby, and which is incorporated by reference herein in its entirety.

FIELD

The present application relates to surgical knee replacement and instruments used therewith.

BACKGROUND

A knee replacement procedure (e.g., knee arthroplasty) is used to repair or replace damaged bone or damaged tissue in a patient knee joint. A knee arthroplasty includes repairing or replacing damaged or diseased articular surfaces of the tibia or femur. The arthroplasty procedure may include cutting (e.g., resecting) one or more articular surfaces of the tibia and femur and replacing a portion of each articular surface with a prosthesis (e.g., articular surface implant). A total knee arthroplasty (TKA) may be used to repair all articular surfaces of the tibia and femur, whereas a partial knee arthroplasty (PKA) may be used to repair a portion of the articular surfaces of the knee, such as the medial, lateral, or patellofemoral compartment.

The TKA and PKA procedures require precise resections of the tibia and femur. The cut depth for each resection is specific to the patient and each prosthesis. A surgeon may validate a resection depth manually by inserting a trial prosthesis and exercising the knee through various motions. However, this resection validation is subjective, time consuming and subject to errors. What is needed is an improved validation process for the knee arthroplasty.

BRIEF DESCRIPTION OF THE DRAWINGS

FIG. 2 is a perspective view of another example of the instrument for validation and removal of material along one or more resected surfaces of the knee, in accordance with an example of the present application.

FIG. 2A is a cross-sectional view of a first end portion of the instrument of FIG. 2, in accordance with an example of the present application.

FIGS. 3-8 are alternative design configurations of the first end portion of various instruments of similar construction to that of FIG. 2.

FIG. 11 is a highly schematic view of a system with the instrument of FIG. 1 being rotated 90° about an axis from a first position at the viewer's left to a second position at the viewers right, in accordance with examples of the present application.

DETAILED DESCRIPTION

Figure 1:
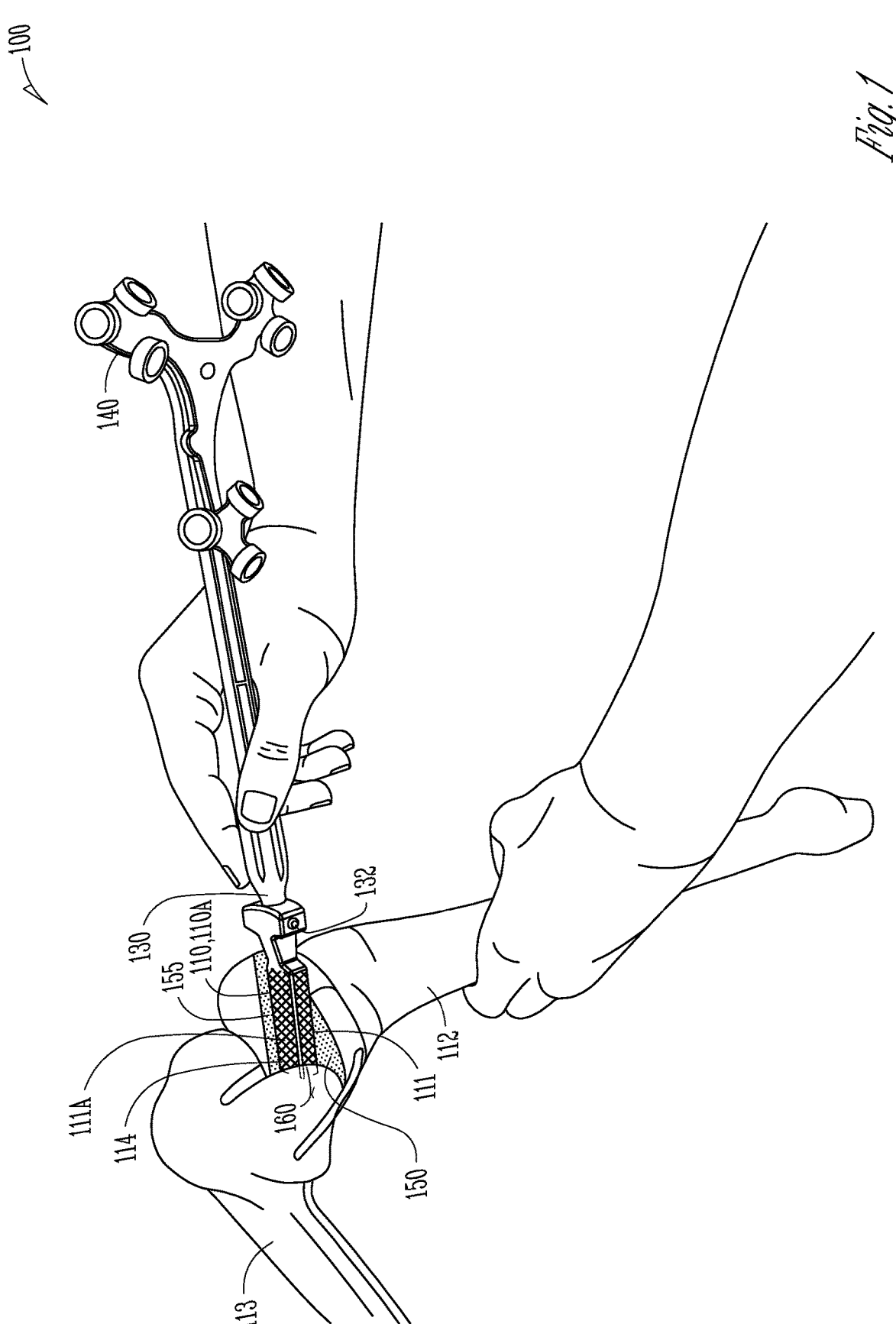
FIG. 1 is a perspective view of an instrument and a system used in a robotic knee arthroplasty, in accordance with an example of the present application.

The present disclosure describes technical solutions to various technical problems occurring in knee arthroplasty procedures. To address some of these technical problems in regards to resection validation, the present subject matter provides a dual use instrument. The instrument can be tracked such as optically for objective measurement of resection depth and other position related information. Additionally, the instrument can include one or more surfaces with a plurality of teeth configured to remove material such as bone. The need to remove material can be the result of undesirable bone fragments remaining on the resected surface(s), an undesirably shaped bone surface(s) and/or an undesirable initial position of the resection surface e.g., an insufficient cut depth, or the like. Providing the dual use instrument presently disclosed can save time, reduce potential for error and reduce surgical complexity as a separate instrument such as a bone file or rasp need not be inserted into the knee joint should validation report an under-resection or unintended angularity. Rather, the same instrument that performs the validation can remain in the knee joint and can be used to perform any additional shaping/removal on the one or more resected surface(s). The instrument can be configured to couple with an optical tracker to facilitate a precise comparison be made between the location of the instrument and a reference location. In this manner, a desired position and/or shape for the one or more resected surface(s) can be achieved. The instrument can be configured to measure and validate each tibial and femoral resection such as in a PKA or can be used in another knee procedure such as a TKA, revision knee arthroplasty or the like.

Several examples of the present application discuss the present invention being used in a PKA. However, this is merely exemplary of a possible procedure that the instruments can be utilized in. In the example PKA surgical procedure, a tibia is resected, the instrument is used to validate the resection, remove any undesired material from the resected surface(s), optionally check flexion gap and/or extension gap. Similarly, the distal femur is resected, and the instrument is again used to validate the resection, remove any undesired material and optionally check one or more gaps. The use of the instrument to validate resections, remove any undesired material from the resected surface(s) and optionally check gap(s) ensures that bone gaps and soft tissue allow for sufficient space for an implant and sufficient space in the postoperative elongated leg. The position of the instrument can be optically tracked in order to validate resections, remove any undesired material from the resected surface(s) and optionally check gap(s).

The instrument may be used with a robotic surgical device. In an example, a robotic surgical device may perform a tibial and/or femoral resection, and the instrument may be used by a surgeon or by the robotic surgical device to validate resections, remove any undesired material from the resected surface(s) and optionally check gap(s). In an example, the robotic surgical device may position resection surgical tools to prepare for the resection, a surgeon may perform a tibial and/or femoral resection, and the instrument may be used by a surgeon or by the robotic surgical device to validate resections, remove any undesired material from the resected surface(s) and optionally check gap(s). The robotic surgical system and tracked knee arthroplasty instrument may use a combination of one or more coordinate systems or tracked positioning systems. In an example, the instrument is tracked using an optical tracking system, the robotic surgical device uses a robotic device coordinate system, and a surgical plan management system translates the instrument position and robotic surgical device position into a common coordinate system viewable by the surgeon.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 1 is a perspective view of a knee arthroplasty system 100, in accordance with some embodiments. The system 100 includes an instrument 110 with a first end portion 110A, a handle 130 and a location tracking device 140. The first end portion 110A includes a least a first articular contact surface 111 that may be placed in contact with one or more resected surfaces (e.g., proximal resection surface 150 of a tibia 112, sagittal resection surface 155 of the tibia 112, and/or a distal resected surface of a femur 113). In an example, proximal tibial resection validation surface 150 can correspond to a distal surface of instrument 110. The first end portion 110A of the instrument 110 can be placed on and abutting the proximal resection 150. Similarly, a sagittal resection validation surface can be on a medial side of instrument 110 an can be placed against and abutting the sagittal resection 155.

The thickness (e.g., proximal-to-distal height) of first end portion 110A as measured from a first major surface to a second opposing major surface separates a proximal surface from the proximal resection validation surface on the distal side (not shown) of the first end portion 110A. This gap validation thickness (a thickness as measured proximal/distal) may be used to validate the gap between the tibial proximal resection 150 and the femoral condyle 160. FIG. 1 shows the gap validation thickness being used to validate the flexion gap while the knee is in flexion, though the gap validation thickness may also be used to validate the extension gap while the knee is in extension.

The first surface 111 can be one of one or more surfaces 111A with a plurality of teeth 114 thereon. Other surfaces of the first end portion 110A can comprise the one or more surfaces 111A including the distal surface, a distal end and/or the medial surface described previously. The plurality of teeth 114 can comprise any features configured for cutting bone. Thus, the first end portion 110A with the plurality of teeth 114 can be configured as a rasp, bone file or other bone cutting tool.

The instrument 110 can include the handle 130 or another feature for grasping to manipulate the first end portion 110A. The first end portion 110A can be integral with or can be a separate component from the handle 130. Indeed, in some examples discussed subsequently the first end portion 110A can be movable (e.g. rotatable) relative to the handle 130. The handle 130 may include grooves, a grip, or other surface to improve the ability of a surgeon to manipulate the instrument 110. The first end portion 110A and/or the handle 130 may include an orientation mechanism (e.g., detent, keying surface) to ensure the first end portion 110A and the handle 130 are attached in a reliable and precise configuration. In an example, the first end portion 110A includes a threaded aperture and the handle 130 includes a threaded socket, and a threaded screw 132 is attached through the first end portion 110A into the handle 130.

The handle 130 is coupled to the location tracking device 140, such as an optical tracker. The tracking device 140 may be used by an optical tracking system to determine the precise location of the instrument 110. In an example, once the first end portion 110A is positioned abutting the proximal resection 150 and/or abutting the sagittal resection 155, the tracking device 140 may be used to validate the proximal tibial resection 150 and/or the sagittal resection 155. The validation of the proximal tibial resection 150 may include determining a position such as a tibial resection cut depth, a *varus*/valgus angle, a resection anterior/posterior slope, or other geometry. The validation of the sagittal resection 155 may include determining a position such as a resection internal-external rotation, a resection medial-lateral offset, or other geometry.

In another example, the position of the first end portion 110A may be tracked to ensure the first end portion 110A is inserted to a sufficient depth between the tibial plateau proximal resection 150 and the native femoral condyle 160 or a distal femoral resection. Cut validations can be performed to determine an under-resection, material on the resection plane, or unintended angularity. Optionally, gap validations can be performed as well. For example, a proximal-distal height of first end portion 110A can be used to validate the gap between the proximal resection 150 and the native femoral condyle 160 or the distal femoral resection. The optical system may determine the position of the tracking device 140 relative to another tracked position, such as relative to an optical tracker fixedly attached to the patient tibia, relative to a registration pointer attached to a robotic arm, or relative to another tracked position.

FIG. 2 is a perspective view of an instrument 210 constructed in a manner similar to that of the instrument 110 of FIG. 1. Thus, the instrument 210 includes a first end portion 210A, a handle 230 and a location tracking device 240. FIG. 2A is a cross-sectional view of the first end portion 210A showing a plurality of teeth 214 that are part of and form the one or more surfaces 211A. The one or more surfaces 211A can include two major surfaces 216 and 218 and two minor surfaces 220 and 222.

The first end portion 210A, the handle 230 and the location tracking device 240 can be arranged along a longitudinal axis LA. The first end portion 210A can include a generally rectangular cross-section. However, other cross-sectional shapes such as square, chamfered rectangle or square, trapezoidal, etc. are contemplated. The two major surfaces 216 and 218 can have substantially a same surface area and can oppose one another on opposite sides of the first end portion 210A. The distance between the two major surfaces 216 and 218 can be a thickness for gap validation as discussed previously. The two minor surfaces 220 and 222 can be arranged substantially orthogonal to and extending between the two major surfaces 216 and 218. The minor surface 220 can oppose the minor surface 222. The distance between the minor surfaces 220 and 222 can also be a thickness for gap validation, for example.

The example of FIG. 2A, the two major surfaces 216 and 218 and the minor surfaces 220 and 222 can have the plurality of teeth 214. For validation purposes, the other tips of the plurality of teeth 214 can form at least part of a first surface 211, which can abut the proximal resection 150 and/or the sagittal resection 155 (FIG. 1). Collectively the tips of the plurality of teeth 214 can form the first surface 211 which is a plane for cut validation. The first surface 211 can be substantially planar as measured across the tips of the plurality of teeth 214. In the example of FIG. 2A, any one or combination of the two major surfaces 216 and 218 and the minor surfaces 220 and 222 can be positioned as desired relative to the tibia and/or femur to serve as the at least the first surface 211 for validation. Additionally, any one or combination of the two major surfaces 216 and 218 and the minor surfaces 220 and 222 can be positioned (or re-positioned) as desired relative to the tibia and/or femur to serve as material removal surface(s) using the plurality of teeth 214. The plurality of teeth 214 can allow the instrument 210 to be manipulated to remove bone and/or other tissue from the tibia and/or femur.

FIG. 3 is a cross-section that shows another configuration for an instrument 310 with a first end portion 310A. The first end portion 310A can have a plurality of teeth 314 that are part of and form one or more surfaces 311A. The one or more surfaces 311A can include two major surfaces 316 and 318 and two minor surfaces 320 and 322. As shown in the example of FIG. 3, the two minor surfaces 320 and 322 can have the plurality of teeth 314. The two major surfaces 316 and 318 can be substantially planar or can have another shape as desired. One or both of the two major surfaces 316 and/or 318 can be used for validation. If, when validation is attempted, and it is determined that a position of one or more of the resected surfaces is incorrect based upon a tracked position of the instrument 310, the first end portion 310A and/or the entire instrument 310 can be rotated 90° (such as about the longitudinal axis LA of FIG. 2) from the position of FIG. 3 to allow the plurality of teeth 314 to abut the resected surface and the instrument 310 can be manipulated to remove bone from the resected surface.

FIG. 4 is a cross-section that shows another configuration for an instrument 410 with a first end portion 410A. The first end portion 410A can have a plurality of teeth 414 that are part of and form one or more surfaces 411A. The one or more surfaces 411A can include two major surfaces 416 and 418 and two minor surfaces 420 and 422. As shown in FIG. 4, the two major surfaces 416 and 418 can have the plurality of teeth 414. The two minor surfaces 420 and 422 can be substantially planar or can have another shape as desired. One or both of the two minor surfaces 420 and/or 422 can be used for validation. Alternatively, one or both of the two major surfaces 416 and/or 418 can be used for validation. If, when validation is attempted using one of the minor surfaces 420 and/or 422, and it is determined that a position of one or more of the resected surfaces is incorrect based upon a tracked position of the instrument 410, the first end portion 410A and/or the entire instrument 410 can be rotated 90° (such as about the longitudinal axis LA of FIG. 2) from the position of FIG. 4 to allow the plurality of teeth 414 to abut the resected surface and the instrument 410 can be manipulated to remove bone from the resected surface. The example of FIG. 4 additionally allows the physician to select a size and/or shape for the plurality of teeth 414 to be selected with a direction of rotation of the instrument 410 or part of the instrument 410 (e.g., the first end portion 410A). In particular, the plurality of teeth 414A of the first major surface 416 differ in configuration than the plurality of teeth 414B of the second major surface 418. If a large amount of material needs to be removed, the larger teeth 414A can be selected by rotating and abutting against the resected surface. If a smaller amount of material is desired to be removed, smaller teeth 414B can be positioned to abut the resected surface and the smaller teeth 414B can be utilized.

FIGS. 5-8 are cross-sections of first end portions of instruments according to further configurations that include chamfer surface(s). The first end portion 510A of the instrument 510 of FIG. 5 has a plurality of teeth 514 positioned on and forming part of one or more surfaces 511A including one or more chamfer surfaces 524 that connect between the major surfaces 516 and 518 and the minor surfaces 520 and 522. The first end portion 610A of the instrument 610 of FIG. 6 has a plurality of teeth 614 positioned on and forming all or part of minor surfaces 620 and 622, similar to the configuration of FIG. 3 discussed previously. The first end portion 710A of the instrument 710 of FIG. 7 can have a plurality of teeth 714 positioned on and forming all or part of major surfaces 716 and 718, similar to the configuration of FIG. 4 discussed previously. FIG. 8 shows an first end portion 810A of an instrument 810 that has a plurality of teeth 814 positioned on and forming all or part of only one of the major surfaces 816 and 818, the second major surface 818. Such a configuration allows the first major surface 816 to be used for validation, for example, while the second major surface 818 with the plurality of teeth 814 can be used for removal of undesired material. The entirety of the instrument 810 or part of the instrument 810 (e.g., the first end portion 810A) can be rotated 180° to abut the second major surface 818 with a resected surface that had previously been abutted by the first major surface 816 for validation.

Figures 9A, 9B:
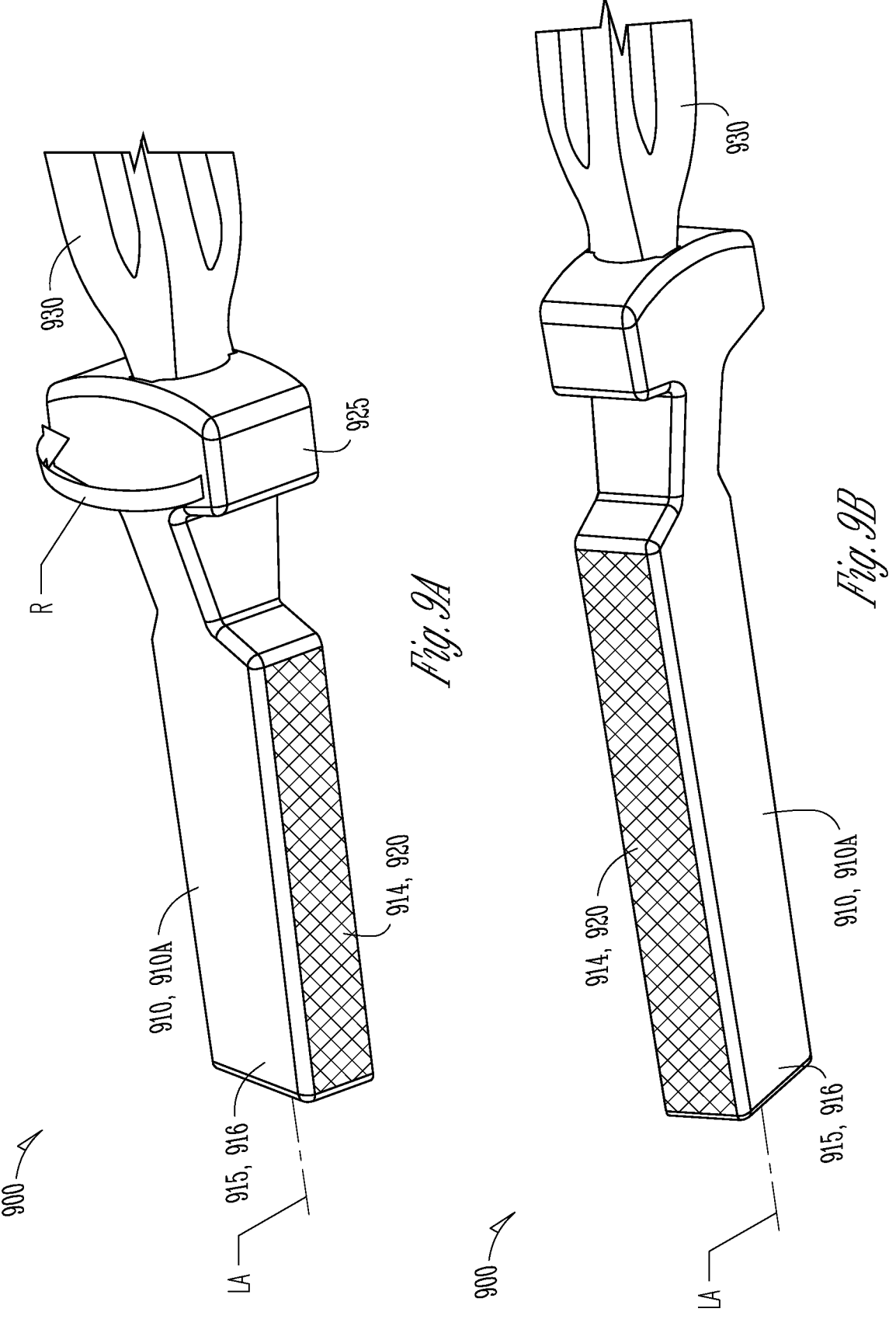
FIGS. 9A and 9B are perspective views of the first end portion of another instrument similar to that of FIG. 1, with the first end portion of the instrument being rotated 90° about an axis from a first position of FIG. 9A to a second position of FIG. 9B, in accordance with examples of the present application.

FIGS. 9A and 9B are perspective views of part of a system 900 of similar construction to the system 100 discussed previously. The system 900 includes an instrument 910 with a first end portion 910A and a handle 930.

The first end portion 910A can include at least one minor surface 920 with a plurality of teeth 914 configured in the manner previously discussed. At least one major surface 916 of the first end portion 910A does not have the plurality of teeth 914 but is substantially planar along an extent thereof. FIG. 9A shows the first end portion 910A in a first position such as abutting a resected surface for validation. If validation is not achieved (e.g., a position of the resected surface is incorrect as result of undesirable bone fragments remaining on the resected surface(s), an undesirably shaped bone surface(s) and/or an undesirable initial position of the resection surface), the first end portion 910A can be rotated 90° or 180° as indicated by arrow R about a longitudinal axis LA relative to the handle 930 to a second position as shown in FIG. 9B. In the second position of FIG. 9B, the plurality of teeth 914 can be used to remove material from the resected surface. The first end portion 910A can then be rotated back to the first position of FIG. 9A and validation can be attempted as described above with at least one of the major surfaces of the first end portion 910A abutting the resected surface.

As shown in FIG. 9A, a posterior portion 925 of the first end portion 910A may be thicker than a distal portion 915. These relatively different thicknesses may be used to validate different gap sizes, such as validating a posterior gap on a posterior portion of a tibial plateau resection and a larger anterior gap on an anterior portion of the tibial plateau resection. Additionally or alternatively, the posterior portion 925 may be wider than the distal portion 915 to provide a mechanical stop, such as by providing a stop against an anterior tibial surface when inserted between the tibial proximal resection 150 (FIG. 1) and the femoral condyle 160 (FIG. 1).

Figure 10:
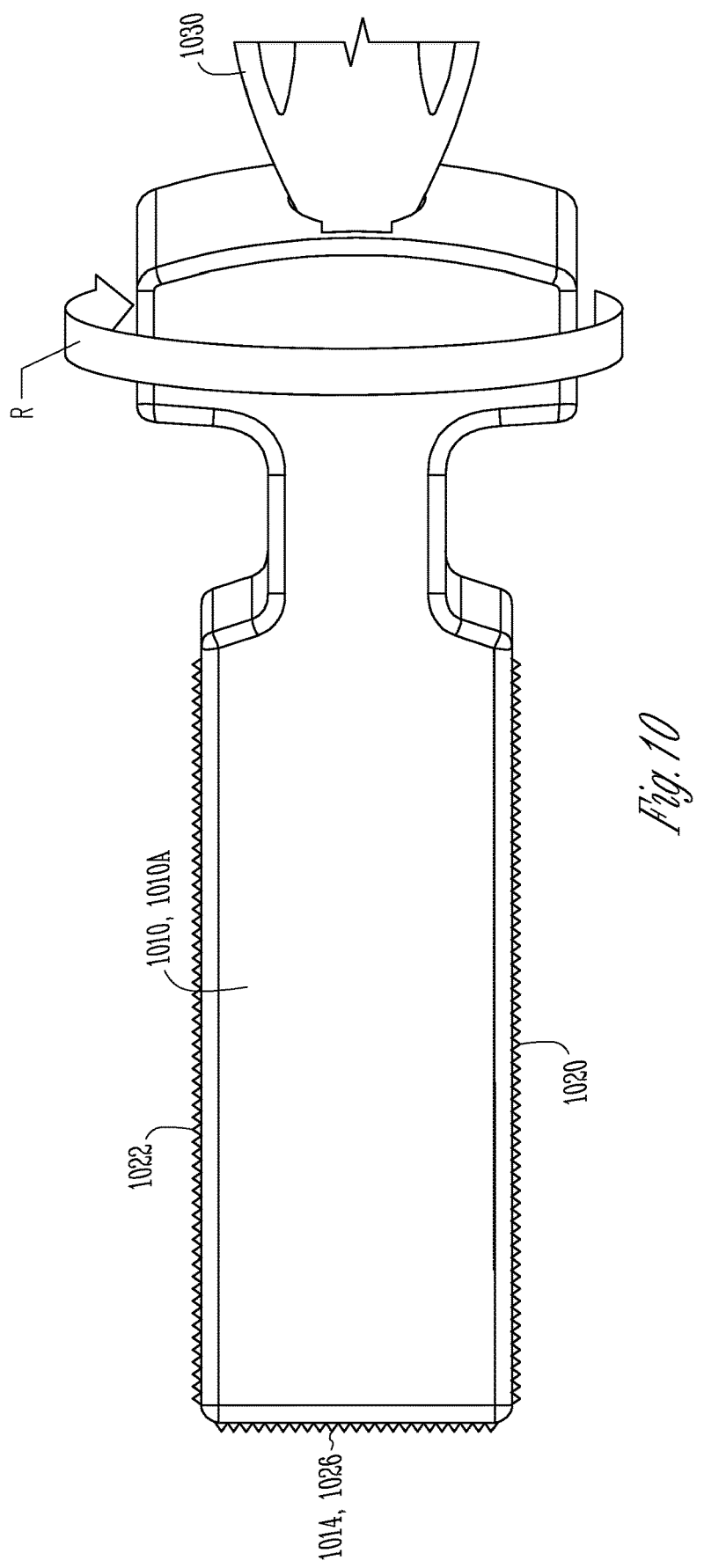
FIG. 10 is a plan view of the first end portion of yet another instrument, in accordance with an example of the present application.

FIG. 10 shows an instrument 1010 with a first end portion 1010A and handle 1030 similar to those described in FIGS. 1, 9A and 9B. However, the first end portion 1010A includes a plurality of teeth 1014 at a distal end surface 1026 in addition to the minor surfaces 1020 and 1022. The first end portion 1010A can optionally be rotated relative to the handle 1030 in a manner described previously in regards to FIGS. 9A and 9B.

FIG. 11 is a schematic view of an instrument 1110 having a construction identical to the instrument 210 of FIG. 2. FIG. 11 illustrates the entire instrument 1110 rotated 90° from a first position 1102 about the longitudinal axis LA (indicated by arrow R) to a second position 1104. FIG. 11 illustrates a system 1100 where, due to rotation of a location tracking device 1140 from the first position to the second position, a second optical device 1150B is used in alternative to a first optical device 1150A, which was used when the location tracking device 1140 was in the first position. Rotation of the entire instrument 1110 can be for validation, referencing, checking one or more gap(s) or to remove material as discussed previously.

Figure 12:
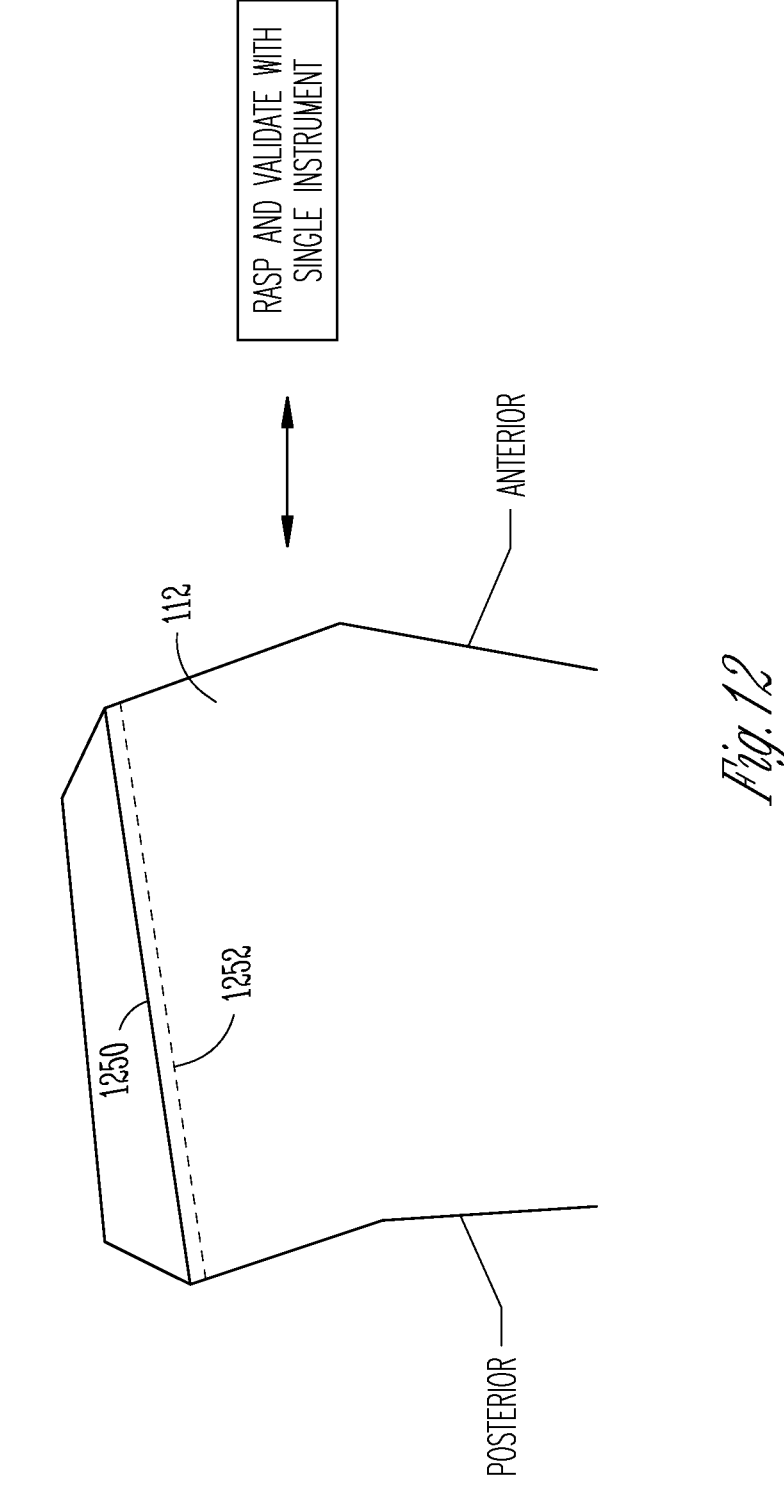
FIG. 12 is a tibial resection diagram and system where the initial proximal resection surface has an insufficient depth upon attempting validation necessitating a removal of additional material, in accordance with an example of the present application.

FIG. 12 is a highly schematic view of a tibial resection diagram and a system 1200 for validation and removal of material using one of the instruments discussed previously in reference to FIGS. 1-11. As shown in FIG. 12, a surgeon or robot may perform a primary cut to form a proximal resected surface 1250 on the tibia 112. Such proximal resection can be for a TKA, for example. If the position (depth and/or slope) of the primary cut (e.g., initial tibial resection) is determined to be improper upon attempted validation using the one of the instruments described previously, this necessitates additional bone removal using the plurality of teeth of the instrument to achieve a desired secondary resected surface 1252 (indicated with dashed line). The present techniques also contemplate a change to the slope/flexion-extension, varus-valgus or internal-external rotation of a resection can be made in some cases rather than simply a removal of material to a different depth along the same orientation as the primary cut.

Figure 13:
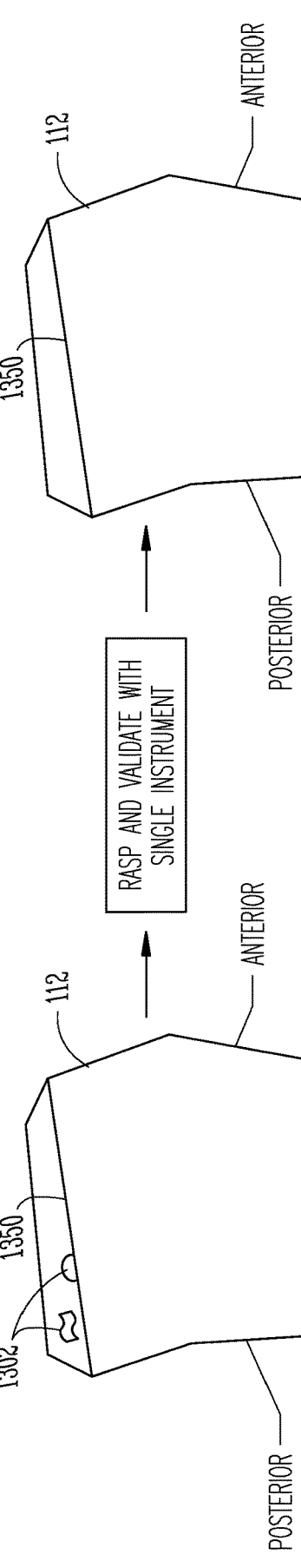
FIG. 13 is a tibial resection diagram and system where the initial proximal resection surface has material(s) that interfere with validation necessitating a removal of the material, in accordance with an example of the present application.

FIG. 13 is a highly schematic view of a tibial resection diagram and a system 1300 for validation and removal of material using one of the instruments discussed previously in reference to FIGS. 1-11. As shown in FIG. 13, a surgeon or robot may perform a primary cut to form a proximal resected surface 1350 on the tibia 112. However, the position of the proximal resected surface 1350 is determined to improper upon attempted validation using one of the instruments described previously. This can be due to undesired material 1302 (e.g. chunks or bits of bone) on the proximal resected surface 1350 on the tibia 112 that did not allow a correct validation position for the instrument to be achieved. The instrument is then used to remove the undesired material 1302 to achieve the proximal resected surface 1350 with a correct position for validation as shown to the viewer's right.

Figure 14:
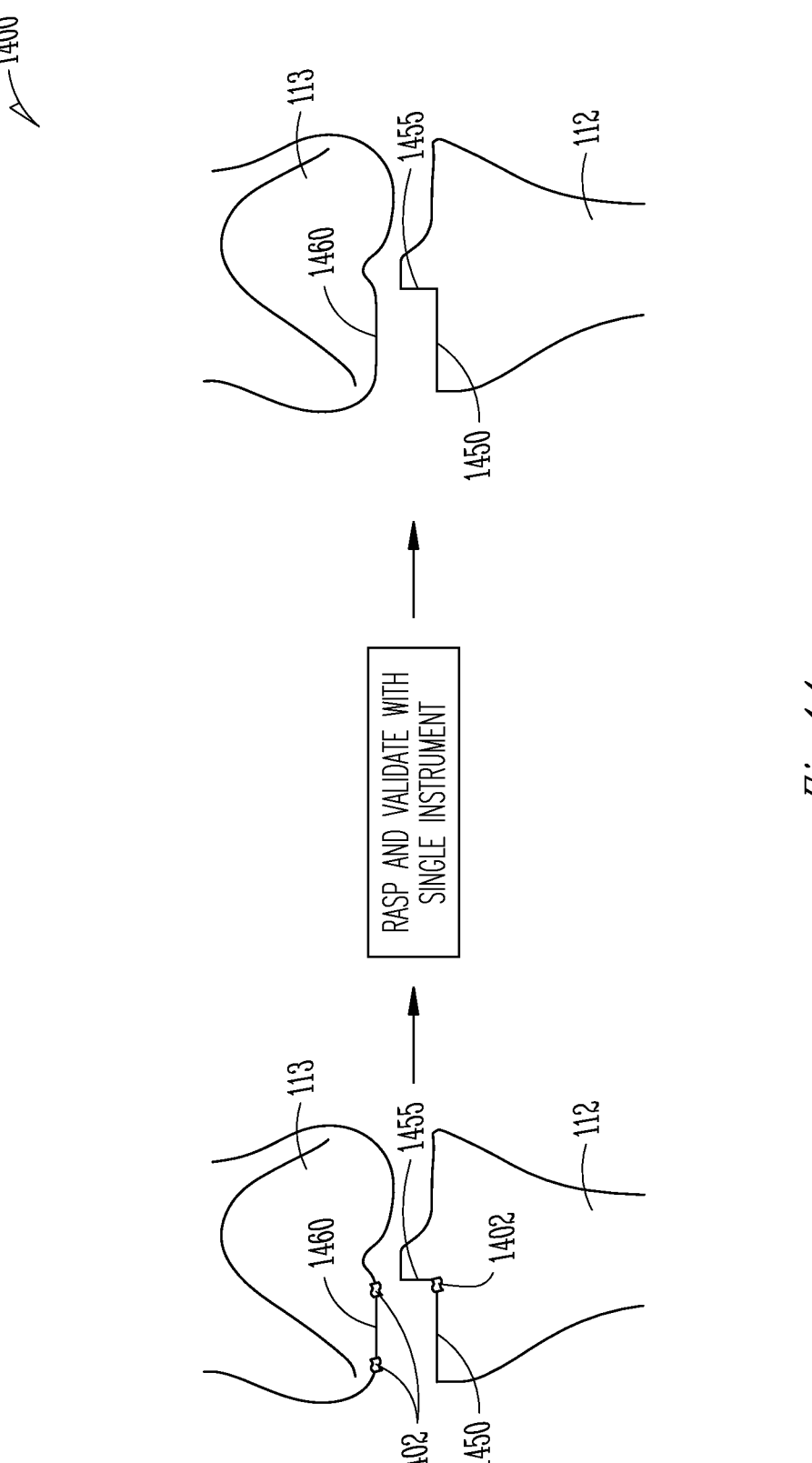
FIG. 14 is a tibiofemoral resection diagram of a femur and tibia for a partial knee arthroplasty (PKA) where the initially resected surfaces have material(s) that interfere with validation necessitating a removal of the material, in accordance with an example of the present application.

FIG. 14 shows a highly schematic view of a PKA resection diagram of the tibia 112 and femur 113 and a system 1400 for validation and removal of material on the tibia 112 and the femur 113 using one of the instruments discussed previously in reference to FIGS. 1-11. As shown in FIG. 14, a surgeon or robot may perform a primary cut to form a proximal resected surface 1450 and a sagittal cut to form a sagittal resected surface 1455 on the tibia 112. Additionally, a distal cut can be performed to form a distal resected surface 1460 on the femur 113. However, the position of one or more of the proximal resected surface 1450, the sagittal resected surface 1455 and the distal resected surface 1460 is determined to be improper upon attempted validation using one of the instruments described previously. This can be due to undesired material 1402 (e.g. chunks or bits of bone) on the one or more of the proximal resected surface 1450, the sagittal resected surface 1455 and the distal resected surface 1460 that did not allow a correct validation position for the instrument to be achieved. The instrument is then used to remove the undesired material 1402 to achieve the desired position for one or more of the proximal resected surface 1450, the sagittal resected surface 1455 and/or the distal resected surface 1460 as shown to the viewer's right.

Figure 15:
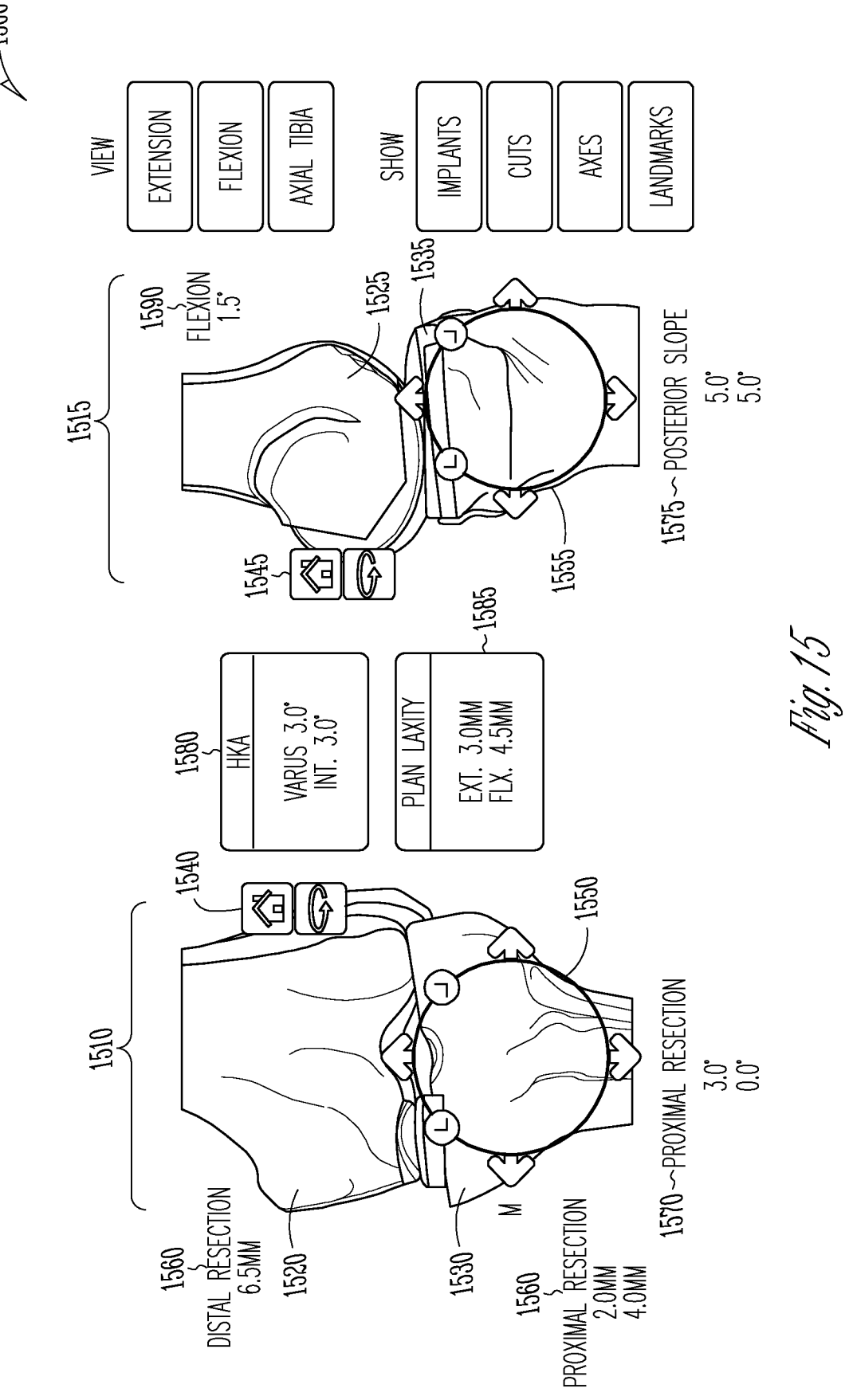
FIG. 15 is a diagram of a graphical user interface (GUI) used such as during a robotic knee arthroplasty, in accordance with an example of the present application.

FIG. 15 is a diagram of a knee arthroplasty graphical user interface (GUI) 1500, in accordance with some embodiments. GUI 1500 may be used to display information about planned or measured arthroplasty resection depths or angles. GUI 1500 may include an anterior view 1510 of the femoral condyle 1520 and the proximal tibia 1530. Similarly, GUI 1500 may include a medial view 1515 of the femoral condyle 1525 and the proximal tibia 1535. The anterior view 1510 may have an associated anterior view control 1540, and the medial view 1515 may have an associated medial view control 1545, which may be used to rotate the view of the femur and tibia displayed within GUI 1500. The anterior view 1510 may have an associated anterior tibial control 1550, and the medial view 1515 may have an associated medial tibial control 1555, which may be used to change the flexion angle or modify tibial slope or resection. GUI 1500 may also provide information about distal resection depth 1560, proximal resection depth 1565, proximal resection slope angles 1570, posterior slope angles 1575, hip-knee-ankle (HKA) axis angles 1580, plan laxity measurements 1585, and a flexion angle 1590.

The display of information, bone views, or other portions within GUI 1500 may be modified to indicate whether one or more steps in the knee arthroplasty surgical procedure have been completed. For example, the proximal resection depth 1565 may be presented in a first color to indicate a sufficient resection depth, and the proximal tibia 1530 and proximal resection angle 1570 may be presented in a second color to indicate additional surgical procedure steps are needed to provide the planned resection slope. In another example, the proximal resection depth 1565 may be presented in a first color to indicate the depth is based on a depth validated by an arthroplasty validation instrument, and the proximal tibia 1530 and proximal resection angle 1570 may be presented in a second color to indicate the displayed resection slope angle is using outdated information.

Figure 16:
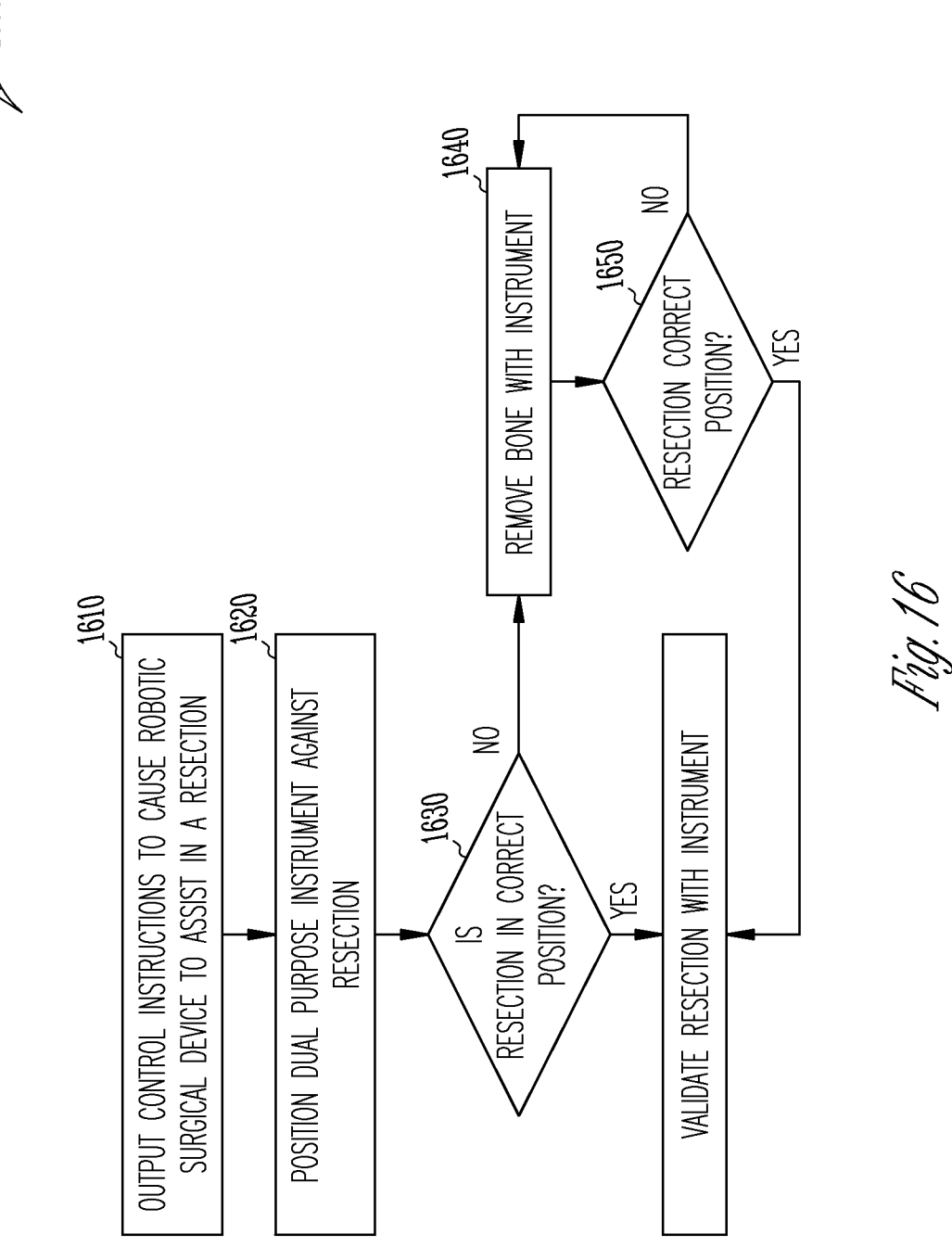
FIG. 16 is a flow chart showing a knee arthroplasty technique, in accordance with an example of the present application.

FIG. 16 illustrates a flow chart showing a knee arthroplasty technique 1600, in accordance with some embodiments. Technique 1600 may include outputting 1610 control instructions to cause a robotic surgical device to assist in a resection of a patient tibia and/or femur. The resection may include a tibial plateau resection, which may include forming a proximal resected surface and a sagittal resected surface.

Technique 1600 includes positioning 1620 an instrument to contact at least one of the resected surfaces on the tibia and/or femur. Positioning of the instrument may include outputting control instructions to cause the robotic surgical device to position the instrument. Technique 1600 may include a surgeon positioning 1620 the instrument and receiving a validation initiation input from the surgeon. The validation input may initiate the validation of the one or more resected surfaces. In particular, positioning 1620 the instrument can have a first end portion in situ in the knee with at least a first surface contacting the one or more resected surfaces. The first end portion can include one or more surfaces with a plurality of teeth configured to remove material from the one or more resected surfaces.

The technique 1600 includes attempting validation 1630, using processing circuitry of the robotic surgical device, a position of the one or more resected surfaces based on a tracked validation position of an optical tracker coupled to the instrument with the first end portion remaining in situ contacting the at least one of the resected surfaces. The technique 1600 such as with the validation 1630 includes indicating with a display if the position of the one or more resected surfaces is one of incorrect or correct based upon the validation.

If the position of the one or more resected surfaces in incorrect, the technique 1600 includes removing 1640 the material from the one or more resected surfaces using the plurality of teeth of the first end portion. The technique 1600 includes re-validation 1650 after the removing, using the processing circuitry of the robotic surgical device, the position of the one or more resected surfaces based on the tracked validation position of the optical tracker of the instrument with the first end portion remaining in situ contacting the at least one of the resected surfaces. The re-validation 1650 includes indicating with the display if the position of the one or more resected surfaces is one of incorrect or correct based upon the re-validation.

The one or more resected surfaces can include one or more of a sagittal tibial resection of the tibia, a distal femoral resection of a femur or a proximal tibial resection of the tibia. The technique 1600 can include rotating part or all of the instrument one of 90° or 180° about a longitudinal axis of the instrument prior to the removing the material from the one or more resected surfaces using the plurality of teeth. The rotating occurs prior to re-validating the tracked validation position of the optical tracker is reoriented and further comprising imaging the optical tracker with a second imaging device. The one or more surfaces with the plurality of teeth can include at least one of two major surfaces or at least one of two minor surfaces of the first end portion. The at least the first surface can include the one or more surfaces with the plurality of teeth. The technique 1600 can include validating a gap between the femur and the tibia with a thickness of the first end portion.

Technique 1600 may include comparing the validation position of the instrument against a tracked tibial or femur position. The tracked tibial or femur position may be based on an optical tibial tracker fixedly attached to the patient tibia or patient femur. The tracked position may be based on a registration position of a registration pointer, where the registration pointer is fixedly attached to a robotic arm of the robotic surgical device.

Figure 17:
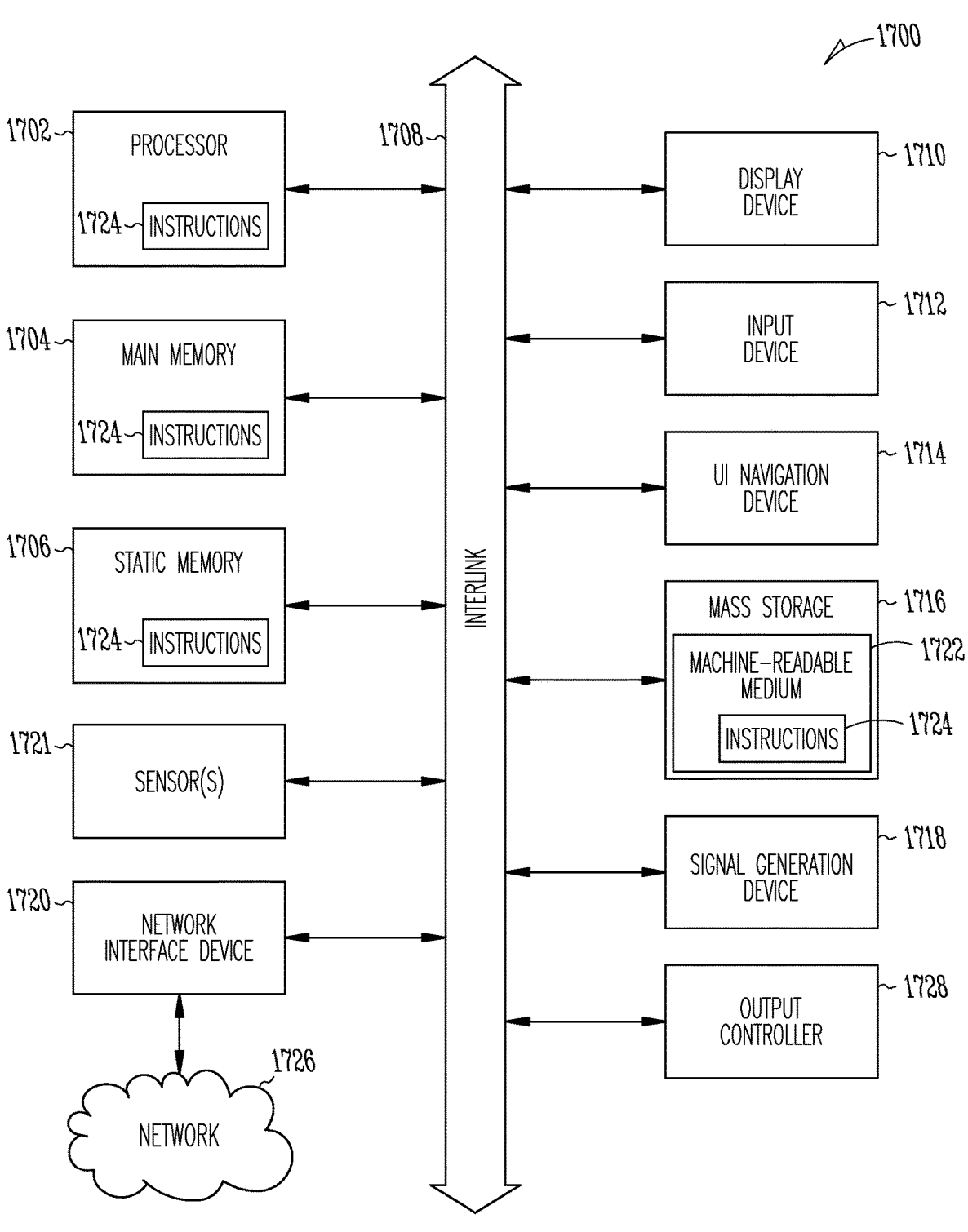
FIG. 17 illustrates an example of a block diagram of a machine upon which any one or more of the techniques (e.g., methodologies) discussed herein may perform in accordance with some embodiments.

FIG. 17 illustrates an example of a block diagram of a machine 1700 upon which any one or more of the techniques (e.g., methodologies) discussed herein may perform in accordance with some embodiments. In alternative embodiments, the machine 1700 may operate as a standalone device or may be connected (e.g., networked) to other machines. In a networked deployment, the machine 1700 may operate in the capacity of a server machine, a client machine, or both in server-client network environments. The machine 1700 may be a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the execution units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 1700 may include a hardware processor 1702 (e.g., a central processing unit (CPU), a graphics processing unit (GPU), a hardware processor core, or any combination thereof), a main memory 1704 and a static memory 1706, some or all of which may communicate with each other via an interlink (e.g., bus) 1708. The machine 1700 may further include a display unit 1710, an alphanumeric input device 1712 (e.g., a keyboard), and a user interface (UI) navigation device 1714 (e.g., a mouse). In an example, the display unit 1710, alphanumeric input device 1712 and UI navigation device 1714 may be a touch screen display. The display unit 1710 may include goggles, glasses, an augmented reality (AR) display, a virtual reality (VR) display, or another display component. For example, the display unit may be worn on a head of a user and may provide a heads-up-display to the user. The alphanumeric input device 1712 may include a virtual keyboard (e.g., a keyboard displayed virtually in a VR or AR setting.

The machine 1700 may additionally include a storage device (e.g., drive unit) 1716, a signal generation device 1718 (e.g., a speaker), a network interface device 1720, and one or more sensors 1721, such as a global positioning system (GPS) sensor, compass, accelerometer, or other sensor. The machine 1700 may include an output controller 1728, such as a serial (e.g., universal serial bus (USB), parallel, or other wired or wireless (e.g., infrared (IR), near field communication (NFC), etc.) connection to communicate or control one or more peripheral devices.

The storage device 1716 may include a machine readable medium 1722 that is non-transitory on which is stored one or more sets of data structures or instructions 1724 (e.g., software) embodying or utilized by any one or more of the techniques or functions described herein. The instructions 1724 may also reside, completely or at least partially, within the main memory 1704, within static memory 1706, or within the hardware processor 1702 during execution thereof by the machine 1700. In an example, one or any combination of the hardware processor 1702, the main memory 1704, the static memory 1706, or the storage device 1716 may constitute machine readable media.

While the machine readable medium 1722 is illustrated as a single medium, the term "machine readable medium" may include a single medium or multiple media (e.g., a centralized or distributed database, or associated caches and servers) configured to store the one or more instructions 1724.

The term "machine readable medium" may include any medium that is capable of storing, encoding, or carrying instructions for execution by the machine 1700 and that cause the machine 1700 to perform any one or more of the techniques of the present disclosure, or that is capable of storing, encoding, or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1724 may further be transmitted or received over a communications network 1726 using a transmission medium via the network interface device 1720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, as the personal area network family of standards known as Bluetooth® that are promulgated by the Bluetooth Special Interest Group, peer-to-peer (P2P) networks, among others. In an example, the network interface device 1720 may include one or more physical jacks (e.g., Ethernet, coaxial, or phone jacks) or one or more antennas to connect to the communications network 1726. In an example, the network interface device 1720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 1700, and includes digital or analog communications signals or other intangible medium to facilitate communication of such software.

Figure 18:
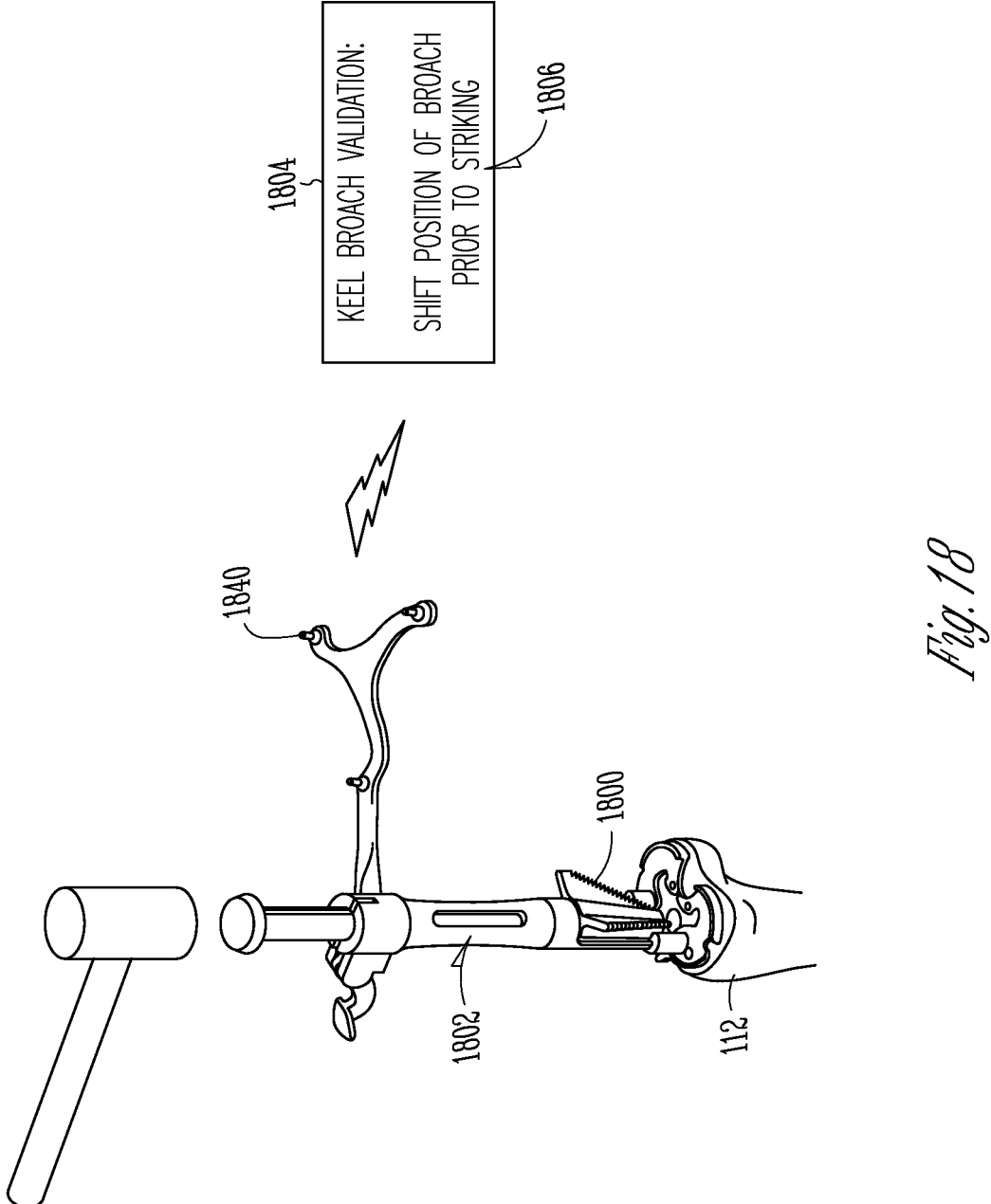
FIGS. 18 and 19 show principles of the present application applied to broaches.

FIG. 18 shows an example of a tibial keel broach 1800 and instrument 1802 such as a slap hammer or other tool used for insertion of the tibial keel broach 1800 into the tibia 112. The present application contemplates one or more validations can be performed on the tibial keel broach 1800 in a manner similar to the resection validations discussed above. As an example, the instrument 1802 can be coupled to a location tracking device 1840 constructed in a manner similar to those previously discussed. An optical system may determine the position of the tracking device 1840 relative to another tracked position, such as relative to an optical tracker fixedly attached to the patient tibia, relative to a registration pointer attached to a robotic arm, or relative to another tracked position. The optical system can be part of a CAS or robotic surgical system that can provide a display 1804 with instructions 1806 to the surgeon (e.g., "insufficient broach depth, strike again with mallet", "shift position of broach anterior-posterior prior to striking", or "shift position of broach medial-lateral prior to striking"). The surgeon can follow the instructions 1806 for validation of broaching performed on the tibia.

Figure 19:
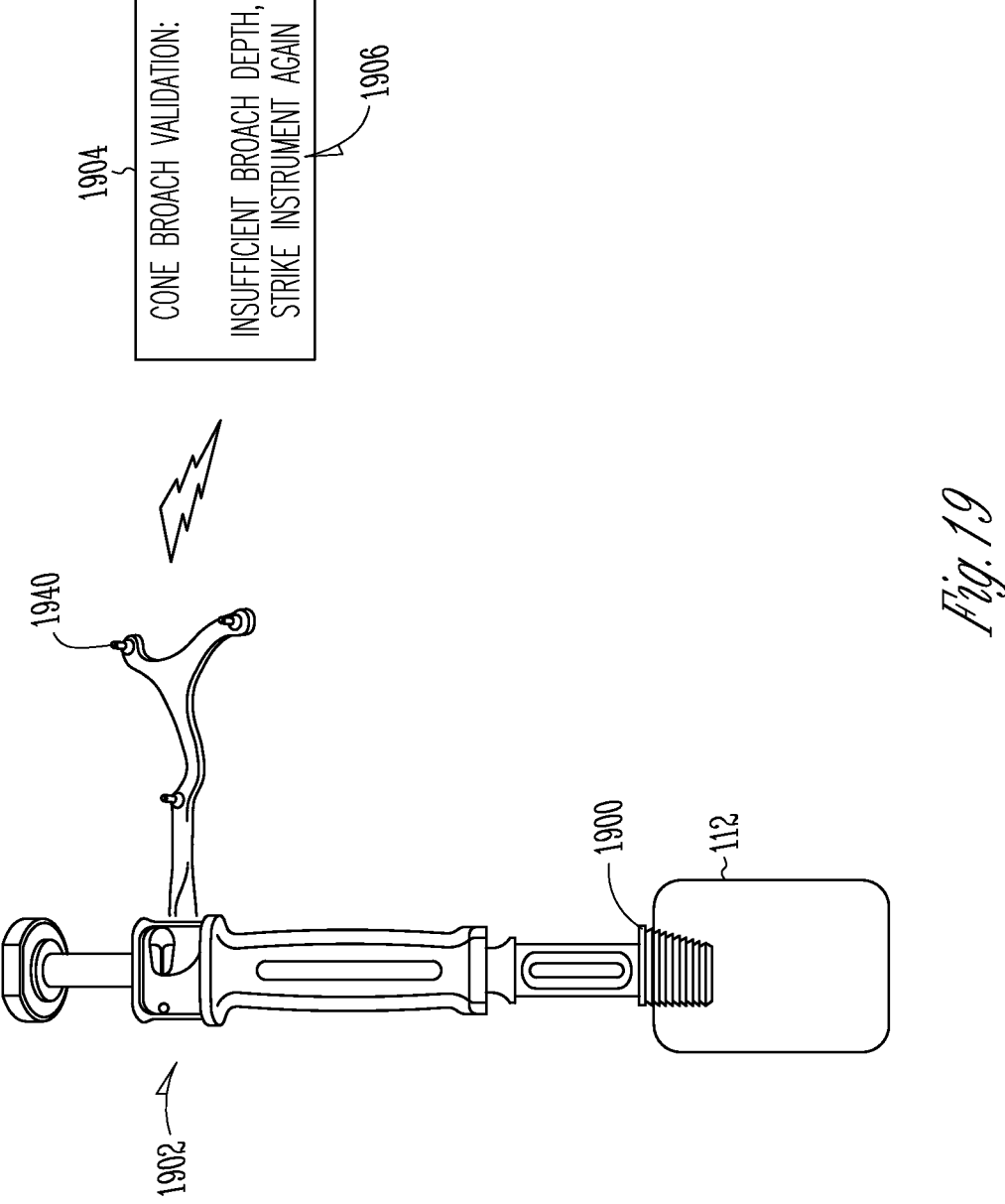

FIG. 19 shows another example of a tibial cone broach 1900 and instrument 1902 such as a slap hammer or other tool used for insertion of the tibial cone broach 1900 into the tibia 112. The present application contemplates one or more validations can be performed on the tibial cone broach 1900 in a manner similar to the resection validations discussed above. As an example, the instrument 1902 can be coupled to a location tracking device 1940 constructed in a manner similar to those previously discussed. An optical system may determine the position of the tracking device 1940 relative to another tracked position, such as relative to an optical tracker fixedly attached to the patient tibia, relative to a registration pointer attached to a robotic arm, or relative to another tracked position. The optical system can be part of a CAS or robotic surgical system that can provide a display 1904 with instructions 1906 to the surgeon (e.g., "insufficient broach depth, strike again with mallet", "shift position of broach anterior-posterior prior to striking", or "shift position of broach medial-lateral prior to striking"). The surgeon can follow the instructions 1806 for validation of broaching performed on the tibia.

Each of the following non-limiting examples (referred to as aspects and techniques below) may stand on its own, or may be combined in various permutations or combinations with one or more of the other examples. Elements of the examples are entirely optional and can be combined in any combination between the different examples listed below.

In some aspects, the techniques described herein relate to an instrument for an arthroplasty of a knee including: a first end portion configured as a validation device having at least a first surface configured to validate a first resected surface of a bone of the knee, wherein the first end portion has one or more surfaces with a plurality of teeth configured to remove material from the first resected surface; a handle portion coupled to the first end portion; and an optical tracker coupled to the handle portion.

In some aspects, the techniques described herein relate to an instrument, wherein the first surface includes the one or more surfaces with the plurality of teeth.

In some aspects, the techniques described herein relate to an instrument, wherein the first surface includes at least one of two major surfaces or at least one of two minor surfaces of the first end portion.

In some aspects, the techniques described herein relate to an instrument, wherein the one or more surfaces with the plurality of teeth include at least one of the two major surfaces or at least one of the two minor surfaces of the first end portion.

In some aspects, the techniques described herein relate to an instrument, wherein the one or more surfaces with the plurality of teeth include one or more chamfer surfaces of the first end portion.

In some aspects, the techniques described herein relate to an instrument, wherein the first end portion is rotatably coupled to the handle portion and is configured to rotate about an axis from a first position to a second position that is one of 90° or 180° rotationally offset from the first position.

In some aspects, the techniques described herein relate to an instrument, wherein the first end portion is configured as a partial knee arthroplasty (PKA) validation device with the first surface configured to abut and validate a sagittal tibial resection of a tibia and at least a second surface configured to abut and validate one of a distal femoral resection of a femur or a proximal tibial resection of the tibia.

In some aspects, the techniques described herein relate to an instrument, wherein the first end portion has a thickness as measured between the first surface and an opposing surface configured to validate a gap between the bone and a second bone of the knee.

In some aspects, the techniques described herein relate to a validation method for intraoperative validation of one or more resected surfaces of a knee during an arthroplasty, the method including: outputting control instructions to cause a robotic surgical device to assist in a resection of one or both of a tibia or a femur; positioning an instrument with a first end portion in situ in the knee with at least a first surface contacting the one or more resected surfaces, wherein the first end portion includes one or more surfaces with a plurality of teeth configured to remove material from the one or more resected surfaces; validating, using processing circuitry of the robotic surgical device, a position of the one or more resected surfaces based on a tracked validation position of an optical tracker coupled to the instrument with the first end portion remaining in situ contacting the at least one of the resected surfaces; indicating with a display if the position of the one or more resected surfaces is one of incorrect or correct based upon the validation; if the position of the one or more resected surfaces in incorrect, removing the material from the one or more resected surfaces using the plurality of teeth of the first end portion; and re-validating after the removing, using the processing circuitry of the robotic surgical device, the position of the one or more resected surfaces based on the tracked validation position of the optical tracker of the instrument with the first end portion remaining in situ contacting the at least one of the resected surfaces.

In some aspects, the techniques described herein relate to a method, wherein the one or more resected surfaces includes one or more of a sagittal tibial resection of the tibia, a distal femoral resection of the femur or a proximal tibial resection of the tibia.

In some aspects, the techniques described herein relate to a method, further including rotating part or all of the instrument one of 90° or 180° about a longitudinal axis of the instrument prior to the removing the material from the one or more resected surfaces using the plurality of teeth.

In some aspects, the techniques described herein relate to a method, wherein rotating occurs prior to re-validating the tracked validation position of the optical tracker is reoriented and further including imaging the optical tracker with a second imaging device.

In some aspects, the techniques described herein relate to a method, wherein the one or more surfaces with the plurality of teeth includes at least one of two major surfaces or at least one of two minor surfaces of the first end portion.

In some aspects, the techniques described herein relate to a method, wherein the first surface includes the one or more surfaces with the plurality of teeth.

In some aspects, the techniques described herein relate to a method, further including validating a gap between the femur and the tibia with a thickness of the first end portion.

In some aspects, the techniques described herein relate to a system for an arthroplasty of a knee including: a robotic surgical device including processing circuitry, the robotic surgical device to assist in a tibiofemoral joint resection of one or both a tibia or a femur; an instrument having a first end portion positioned in situ in the knee with at least a first surface in contact with one or more resected surfaces of one or both of the tibia or the femur, wherein the first end portion includes one or more surfaces with a plurality of teeth configured to remove material from the one or more resected surfaces; and an optical tracker coupled to the instrument; wherein the processing circuitry of the robotic surgical device displays an indication if a position of the one or more resected surfaces based on a tracked validation position of the optical tracker with the first end portion remaining in situ contacting the at least one of the resected surfaces is correct or incorrect; wherein if the position of the one or more resected surfaces in incorrect, removing the material from the one or more resected surfaces using the plurality of teeth of the first end portion; and wherein, after the removing the material, the processing circuitry of the robotic surgical device displays the indication if the position of the one or more resected surfaces based on a tracked validation position of the optical tracker with the first end portion remaining in situ contacting the one or more of the resected surfaces is correct or incorrect.

In some aspects, the techniques described herein relate to a system, wherein if the position of the one or more of the resected surfaces is correct the processing circuitry of the robotic surgical device triggers an update of the display to indicate completion of validation, and wherein if the position of the one or more resected surfaces is incorrect the processing circuitry of the robotic surgical device triggers a report an under-resection or unintended angularity.

In some aspects, the techniques described herein relate to a system, wherein the one or more resected surfaces includes one or more of a sagittal tibial resection of the tibia, a distal femoral resection of the femur or a proximal tibial resection of the tibia.

In some aspects, the techniques described herein relate to a system, wherein the first surface includes the one or more surfaces with the plurality of teeth.

In some aspects, the techniques described herein relate to a system, wherein the first surface includes at least one of two major surfaces or at least one of two minor surfaces of the first end portion.

In some aspects, the techniques described herein relate to a system, wherein the one or more surfaces with the plurality of teeth include at least one of the two major surfaces or at least one of the two minor surfaces of the first end portion.

In some aspects, the techniques described herein relate to a system, wherein the first end portion is rotatably coupled to a remainder of the instrument and is configured to rotate about an axis from a first position to a second position one of 90° or 180° rotationally offset from the first position.

In some aspects, the techniques described herein relate to a system, wherein the first end portion has a thickness as measured between the first surface and an opposing surface configured to validate a gap between the femur and the tibia of the knee.

In some aspects, the techniques described herein relate to a system, wherein the first surface is substantially planar.

Further Example is at least one machine-readable medium including instructions that, when executed by processing circuitry, cause the processing circuitry to perform operations to implement of any of the Examples.

Further Example is an apparatus comprising means to implement of any of Examples.

Further Example is a system to implement of any of the Examples.

Further Example is a method to implement of any of the Examples.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:

1. A system for an arthroplasty of a knee comprising:
   a robotic surgical device including processing circuitry, the robotic surgical device to assist in a tibiofemoral joint resection of one or both a tibia or a femur;
   an instrument manipulated by the robotic surgical device, the instrument having a first end portion configured to be positioned in situ in the knee with at least a first surface in contact with one or more resected surfaces of one or both of the tibia or the femur, wherein the first end portion includes one or more surfaces with a plurality of teeth configured to remove material from the one or more resected surfaces, wherein the first end portion has a thickness as measured between the first surface and an opposite surface, the thickness configured to validate a gap between the femur and the tibia of the knee; and an optical tracker coupled to the instrument;
   wherein the processing circuitry of the robotic surgical device displays an indication if a position of the one or more resected surfaces based on a tracked validation position of the optical tracker with the first end portion remaining positioned in situ in the knee and the one or more surfaces contacting the one or more resected surfaces is correct or incorrect based upon a tracked position of the instrument;
   wherein if the position of the one or more resected surfaces is incorrect, removing the material from the one or more resected surfaces using the plurality of teeth of the first end portion by actuating the robotic surgical device to manipulate the instrument in the knee; and
   wherein, after the removing the material, the processing circuitry of the robotic surgical device displays the indication if the position of the one or more resected surfaces based on a tracked validation position of the optical tracker with the first end portion remaining in situ in the knee and the one or more surfaces contacting the one or more resected surfaces is correct or incorrect based upon the tracked position of the instrument.

2. The system of claim 1, wherein if the position of the one or more resected surfaces is correct the processing circuitry of the robotic surgical device triggers an update of to display an indication of completion of validation, and wherein if the position of the one or more resected surfaces is incorrect the processing circuitry of the robotic surgical device triggers a report an under-resection or unintended angularity.

3. The system of claim 1, wherein the one or more resected surfaces includes one or more of a sagittal tibial resection of the tibia, a distal femoral resection of the femur or a proximal tibial resection of the tibia.

4. The system of claim 1, wherein the first surface includes the one or more surfaces with the plurality of teeth.

5. The system of claim 1, wherein the first surface includes at least one of two major surfaces or at least one of two minor surfaces of the first end portion, wherein the one or more surfaces with the plurality of teeth include at least one of the two major surfaces or at least one of the two minor surfaces of the first end portion.

6. The system of claim 1, wherein the first end portion is rotatably coupled to a remainder of the instrument and is configured to rotate about an axis from a first position to a second position one of 90° or 180° rotationally offset from the first position.

7. The system of claim 1, wherein the first surface is substantially planar.

* * * * *